United States Patent [19]
Bac et al.

[11] Patent Number: 5,990,058
[45] Date of Patent: Nov. 23, 1999

[54] HAIR HYGIENE PRODUCT OR HAIR TREATMENT PRODUCT FOR MAN OR ANIMALS

[76] Inventors: Elisabeth Bac, 4 rue de Longpont, 92200 Neuilly; Jean-Pierre Benoit, 145 rue Victor Hugo, 14800 Deauville, both of France

[21] Appl. No.: 09/003,161

[22] Filed: Jan. 6, 1998

Related U.S. Application Data

[63] Continuation of application No. PCT/FR96/01058, Jul. 5, 1996.

[30]     Foreign Application Priority Data

Jul. 7, 1995 [FR]   France ................................ 95 08265

[51] Int. Cl.⁶ .............................. C11D 17/00; C11D 3/33; A61K 7/06
[52] U.S. Cl. .................... 510/120; 510/123; 510/125; 510/160; 510/439; 510/446; 510/475; 424/70.1; 424/70.15; 424/70.19; 424/465
[58] Field of Search ..................... 510/120, 123, 510/125, 160, 439, 446, 475; 424/70.1, 70.15, 70.19, 400, 464, 465, 489

[56]           References Cited

U.S. PATENT DOCUMENTS

| | | | |
|---|---|---|---|
| 4,012,341 | 3/1977 | Orshitzer et al. | 510/120 |
| 4,478,734 | 10/1984 | Ogino et al. | 510/490 |
| 4,664,835 | 5/1987 | Grollier et al. | 510/119 |
| 4,707,293 | 11/1987 | Ferro | 510/121 |
| 4,737,362 | 4/1988 | Yoshizumi et al. | 424/94.6 |
| 4,855,130 | 8/1989 | Konrad et al. | 424/70 |
| 4,929,378 | 5/1990 | Morita et al. | 510/130 |
| 5,062,994 | 11/1991 | Imperatori | 510/141 |
| 5,352,387 | 10/1994 | Rahman et al. | 510/496 |
| 5,523,017 | 6/1996 | Moran et al. | 510/447 |
| 5,824,629 | 10/1998 | Petritsch | 510/120 |

FOREIGN PATENT DOCUMENTS

| | | |
|---|---|---|
| 0 091 237 | 10/1983 | European Pat. Off. . |
| 0330435 | 8/1989 | European Pat. Off. . |
| 0 367 926 | 5/1990 | European Pat. Off. . |
| 0 370 969 | 5/1990 | European Pat. Off. . |
| 0 659 341 | 6/1995 | European Pat. Off. . |
| 43 24 358 | 1/1994 | Germany . |
| 02218605 | 8/1990 | Japan . |
| WOA93 07245 | 4/1993 | WIPO . |
| WOA94 12467 | 6/1994 | WIPO . |
| WOA95 15745 | 6/1995 | WIPO . |

OTHER PUBLICATIONS

Römpp Chemie Lexikon, Georg Thieme Verlag, 1989, pp. 3583–3584, XP002016486.

*Primary Examiner*—Lorna M. Douyon
*Attorney, Agent, or Firm*—Henderson & Sturm

[57]           ABSTRACT

A single-dose solid composition useful for cleaning or treating human or animal hair and having a high disintegration rate in water is disclosed. The composition includes at least one surface active agent selected from the group consisting of an anionic surface active agent and a nonionic surface active agent, an amphoteric product and at least one disintegrating agent. The composition has a disintegration time in an aqueous medium selected from the group consisting of water and aqueous solutions of less than about 5 minutes. The disintegrating agent consists essentially of polyvinylpyrrolidone. A method for making said composition is also disclosed.

9 Claims, No Drawings

HAIR HYGIENE PRODUCT OR HAIR TREATMENT PRODUCT FOR MAN OR ANIMALS

This is a continuation, of co-pending PCT application Ser. No. PCT/FR96/01058, filed on Jul. 5. 1996, entitled HAIR HYGIENE PRODUCT OR HAIR TREATMENT PRODUCT FOR MAN OR ANIMALS, the disclosure of which in its entirety is incorporated by reference thereto herein.

The subject of the invention is a hair hygiene product for man or a hair treatment product for man and animals which is provided in a single-dose solid form and which exhibits a high rate of disintegration in water.

Another subject of the invention is the process for manufacturing this product.

Shampoos which are provided in a solid form have already been proposed in the literature.

Thus, U.S. Pat. No. 4,012,341 describes a shampoo bar containing synthetic detergents. However, on the one hand, this bar does not constitute a single dose and, on the other hand and in particular, its rate of dissolution in water is extremely low, since, according to the test employed in this patent for measuring the solubilization of the composition, it takes 20 minutes to dissolve 0.5 gram of product at a stirring rate of 200 revolutions per minute. The solid shampoo described in this patent therefore very clearly resembles a conventional bar of soap.

Patent Application WO 93/07245 also describes a solid bar which can be used as a shampoo and which contains, in addition to a detergent, at least 65% by weight of a polyethylene glycol having an average mole-cular mass of between 5,000 and 10,000. Just like the shampoo bar described in the abovementioned U.S. Pat. No. 4,012,341, this solid bar is manufactured by casting the composition in a mold, removal from the mold being carried out after hardening. No information relating to the solubility of the finished product is given in this patent application. It is possible, at the very most, to divine that the base system is solid, with characteristics of good solubility in hot water. However, everything indicates that, when the solid bar which is described in this patent application is used as a shampoo, it is a shampoo in the same way as a normal soap, solubilization only being obtained very slowly and by virtue in particular of rubbing the solid bar against the hair.

EP Patent 0,330,435 describes, for its part, a solid shampoo bar, characterized in that it is obtained by compacting a detergent provided in the form of needles. It is indicated, in this patent application, that the shampoo bar thus manufactured is readily distinguished from a conventional bar of soap due to the presence of the detergent needles, which remain obvious. Nothing is specifically mentioned as regards the solubility of the product but it is indicated that the latter is used in the manner of a conventional bar of soap.

Patent Application EP 0 370 969 describes a skin cleaning composition comprising at least one pulverulent cleaning substance chosen from anionic, amphoteric, nonionic or cationic cleaning materials in combination with an absorbing powder intended to increase the skin cleaning properties.

The subject of International Application PCT WO 95/15745 is hair washing and care products in the form of compressed tablets containing a base substance which releases, on contact with water, a gas, preferably $CO_2$, which is harmless physiologically and which is preferably provided in the form of a combination comprising at least one carbonate, if appropriate a carbamate, and/or one hydrogen-carbonate and at least one acid, in the solid phase. Moreover, the said compressed tablets contain at least one surface-active agent in the solid phase which is compatible with the skin and the hair, at least one active principle for caring for the skin and/or hair, and at least one stabilizer and/or one aid and/or one additive for compressed tablets or for the manufacture of compressed tablets.

Patent Application EP 0,091,237 relates to a detergent composition possessing good solubility by virtue of the effect of two types of compound.

Shampoos in solid form have thus already been described in the prior art but it turns out that they are all provided in the form of conventional solid bars, similar or identical to bars of soap, and that they are used in the same way, by slow dissolution of part of the solid bar between the hands or against the hair.

In addition to being commonplace, these products suffer from several disadvantages which are essentially due to a lack of practical features when they are used.

Starting from this observation, the Applicants have devised and have succeeded in developing a hair hygiene product which is very comfortable and which exhibits great flexibility in use, and which in addition proves to be very easy to transport and stable on storage, even in a moist atmosphere.

This hair hygiene product can, in addition, be used as a vehicle for dermatological, antiparasitic or cosmetological treatment agents. It can also be used as a hair treatment product for animals and in particular for pets, such as cats and dogs.

The subject of the invention is therefore a hair hygiene product for man or a hair treatment product for man and animals, this product being characterized in that it is provided in single-dose form and in that it has a very short disintegration time in water or in aqueous solutions.

"Hair hygiene product or hair treatment product" is understood to mean in particular, within the context of the present invention, shampoos, conditioners, so-called "2 in 1" shampoos, softeners, shaving products, depilatory products or antilouse, antitick or antiparasitic products in general.

The term single dose is understood to mean, within the context of the present invention, the dose corresponding to a single application of the product. This dose can obviously vary, and be adjusted, according to the specific features of the individuals or of the animals under consideration and/or according to the treatments targeted.

Finally, as regards the disintegration time of the product in water or in aqueous solutions, it is evaluated by a test which is extremely easy to carry out. This test consists in placing the product in a 1000 ml tall form beaker filled with 800 ml of distilled water brought to a temperature of 35° C., stirred at a rate of 400 revolutions per minute by a stirrer of Hanna HI 322 trademark, equipped with a Teflon magnetic bar with a length of 70 mm and a cross section of 9.5 mm, and in measuring the time necessary to obtain complete disintegration, that is to say complete break-up or complete loss of cohesion.

The product in accordance with the invention has, in this test, which will subsequently be denoted "D test", a disintegration time of less than 5 minutes, preferably of less than 3 minutes and more preferably still of less than 2 minutes.

By way of indication, these tests have been carried out on 3.20 g compressed tablets with a diameter of 28 mm, a thickness of 5 mm and a hardness of 8 kg plus or minus 1.

Tests have also been carried out by employing 800 ml of distilled water at 20° C. and 800 ml of distilled water containing 8 g per litre of sodium chloride. Under these novel conditions, the disintegration time of the compressed tablets remains virtually unchanged, which allows it to be concluded that the products according to the invention can also be easily used in seawater.

The products according to the invention are preferably prepared in the form of pellets or compressed tablets, the latter being preferred. They most generally exhibit a diameter varying from approximately 1.5 to approximately 5 cm and a thickness from 2 mm to 10 mm. Their weight most generally lies between 1 and 7 grams, preferably between 2.5 and 5 grams.

The product according to the invention comprises, the percentages being expressed by weight on a dry basis:

from 3 to 30%, preferably from 4 to 24% and more preferably still from 8 to 20% of an anionic surface-active agent and/or of a nonionic surface-active agent, from 6 to 30%, preferably from 9 to 27% and more preferably still from 12 to 22% of an amphoteric product, from 15 to 40%, preferably from 20 to 35% and more preferably still from 22 to 32% of at least one disintegrating agent.

The remainder to 100% is composed, if appropriate, of granulation or compression excipients, fillers, dyes, proteins, lubricating agents, release agents, fragrances, quaternary ammoniums, preserving agents, antioxidants, ionic polymers, chelating or complexing agents, amino acids, trace elements, vitamins, coated or encapsulated essential oils, metal, organic or organometallic salts, or active materials useful in the dermatological, antiparasitic or cosmetological treatments which may be targeted, it being possible for the said active materials to be in the free, granulated, complexed or encapsulated form.

The product in accordance with the invention preferably comprises from 2 to 10%, preferably from 4 to 10%, of glycine and from 8 to 25%, preferably from 10 to 20%, of a granulation or compression excipient.

According to a particularly advantageous embodiment, the disintegrating agent consists of insoluble polyvinylpyrrolidone.

Mention may be made, as anionic or nonionic surface-active products which can be used in the context of the present invention, of, for example, alkylpolyglucosides, alkylolamide sulfosuccinates of fatty acids, and in particular those sold under the trade names Oramix SP 100 and Rewoderm S1333 P by the Companies Seppic and Witco.

Betaine derivatives can be used as amphoteric products.

Recourse may be had, as granulation excipients, to amylaceous products or cellulose products, such as Avicel, and recourse may be had, as direct compression excipients, to sugars or sugar alcohols renowned for their qualities of ability to be compressed. Sorbitol is the preferred direct compression excipient.

As mentioned above, the products according to the invention are preferably prepared in the form of compressed tablets, the latter having a diameter of approximately 1.5 to 5 cm and a weight of approximately 1 to 7 grams. The development of such compressed tablets is difficult, insofar as the surface-active agents and the amphoteric agents present in a large amount in the composition of the products in accordance with the invention lead to the appearance of adhesion phenomena during the compression operation, which can result, in certain cases, in the impossibility of continuing the said operation. Moreover, the need to obtain a very high rate of disintegration of the finished product is a constraint with which it is difficult to comply in the case of compressed tablets. In spite of these difficulties, the Applicants have succeeded in developing compressed tablets which simultaneously satisfy the manufacturing constraints and the constraints of use. These compressed tablets comprise from 8 to 20% of a powdered anionic surface-active agent and/or surface-active agent, such as those sold under the trade names Rewoderm by the Company Witco or the trade name Oramix SP 100 by the Company Seppic, from 12 to 22% of an amphoteric product, such as the product sold under the trade name Rewoteric AMB12 from the Company Witco or such as the product Tego Betaine CKD sold by the Company Goldschmidt, from 22 to 32% of a disintegrating agent consisting essentially of insoluble polyvinylpyrrolidone, such as that sold by the Company BASF under the trade name Kollidon CL, and from 8 to 25% of a direct compression excipient, such as the sorbitol sold by the Company Roquette under the trade name Neosorb P 60 W.

In order to decrease the phenomena of adhesion to the compressing machine, the Applicants have discovered that it is entirely advantageous to encapsulate or to complex the amphoteric agents with products such as cyclodextrins and in particular the β-cyclodextrin of Kleptose trademark sold by the Company Roquette.

The fact that the product according to the invention is provided in a single-dose form has many advantages. Thus, the product can be very easily transported, without any risk of spilling in bags or over personal effects, faults which are unfortunately inherent in conventional products which are provided in liquid form.

The transportation of the product is also facilitated insofar as the consumer can anticipate the amount which he needs for the duration of a journey, which is obviously impossible in the case of a liquid product or in the case of a solid bar. Likewise, the single-dose form does away with the disadvantage arising from the transportation of the product remaining after use. The volumes and weights of these products are therefore substantially reduced during journeys.

The single-dose form also makes it possible to very precisely suit the concentration of active principle or of treatment product according to the individual or to the animal concerned and according to the desired effects, which avoids the use of excessively low or, in contrast, of excessively high amounts of active principle.

The single-dose form also makes it possible to provide, when the treatments are complex and involve several active principles, kits in which the various compressed tablets correspond to different treatments, it being possible for the latter to be successive or simultaneous. Compressed tablets or pellets corresponding to each of these treatments can, if need be, be distinguished by, for example, different colors obtained by the incorporation of dyes.

The high rate of disintegration of the product according to the invention provides, for its part, very great comfort during use. This rate of disintegration must not, however, be too low, in order for the product to have the time to develop the necessary effectiveness. In practice, the rate of disintegration in the D test is thus preferably between 30 seconds and 5 minutes.

This corresponds to a disintegration, during the effective use of the product, of approximately 30 seconds to 2 minutes, in the case, for example, of a shampoo in the form of a compressed tablet with a diameter of 2.8 cm.

It is remarkable to observe that the products in accordance with the invention exhibit, surprisingly and unexpectedly, good stability towards moisture. This was entirely unforeseeable, given the use in the formulation of these products of very hydrophilic compounds, indeed hygroscopic compounds, and given the very high rate of disintegration of the finished products in water or in aqueous solutions.

Due to this stability towards moisture, it is not absolutely necessary to wrap the products individually in watertight materials. This can be a significant economic saving as regards wrapping, it being possible for the compressed tablets to be packaged directly, such as in a closed tube.

Moreover, the stability towards moisture of the products according to the invention makes it possible to include treating agents or active materials which are labile or unstable in water, agents or materials which could not be included in liquid shampoos.

On account of their reduced size and reduced weight, as well as their stability, the products according to the invention can in particular be used in vending machines, in sports halls or swimming pools.

Another subject of the invention is a process for the manufacture of hair hygiene products for man or hair treatment products for man and animals in accordance with the invention.

This process is characterized in that, in a first stage, the various ingredients which are to form part of the composition are dry mixed, this mixing stage optionally being preceded by the micronization or sieving of certain components, and then in that, in a second stage, the product is shaped, this shaping preferably being carried out, in a way known per se, by granulation or by direct compression. The products obtained are then subjected to microbiological and chemical analyses and then wrapped and packaged.

The invention can be better understood by virtue of the following two examples, which are given purely by way of illustration.

EXAMPLE 1

A shampoo in the form of compressed tablets is manufactured according to the following formulation:

Powdered nonionic surfactant, of trade mark Oramix SP 100, sold by Seppic . . . 16%
Amphoteric product composed of cocamidopropyl betaine, sold under the trade mark Tego Betain CK D by the Company Th. Goldschmidt AG . . . 18%
Product sold under the trade mark Monteine WK HP by the Company Seppic . . . 1%
Urea . . . 2%
Sodium caseinate . . . 1%
Titanium oxide . . . 1%
Insoluble polyvinylpyrrolidone sold under the trade mark Kollidon CL by the Company BASF . . . 25%
Modified cellulose gum, known as Sodium croscarmellose, sold under the trade mark Ac-Di-Sol by the Company Seppic . . . 5%
Glycine . . . 6.5%
Dye . . . 0.2%
Fragrance . . . 0.3%
Sorbitol, sold under the trade mark Neosorb P 60 W by the Company Roquette . . . 13%
Wheat fibers, sold under the trade mark Sofabran F 146 by the company Sofalia . . . 2%
Potato starch . . . 5%
Symperonic PE/F68, sold by the company Lambert-Riviere . . . 2%
Cationic polymer sold under the trade mark N Hance 31 96 by the company Hercules . . . 2%

The various components are mixed in several stages in a planetary-type mixer. In a first step, the active principles are mixed with the main excipients and the fragrance is sprayed, then the glycine is incorporated and, finally, the various disintegrating products used are introduced into the mixture. The mixing operation is subsequently continued for approximately half an hour and then the product is compressed by direct compression in a compression machine of the alternating 1B type with the trade mark Frogerais.

The compressed tablet thus obtained exhibits a disintegration time in distilled water of 90 seconds in the D test. It remains stable in a moist atmosphere.

The disintegration time in normal use, under a shower, is approximately 1 minute.

EXAMPLE 2

A shampoo in the form of a compressed tablet was prepared according to the same procedure as that described in Example 1, the formulation being as follows:

Surfactant sold by the Company Witco under the trade mark Rewoderm S 13 33 P, which is a Disodium Ricinoleamido MEA-Sulfosuccinate . . . 16%
Amphoteric product sold by the Company Witco under the trade mark Rewoteric A M B 12 P which is a Lauramidopropyl Betaine . . . 18% Product sold under the trade mark Monteine WK HP by the Company Seppic . . . 1%
Urea . . . 2%
Sodium caseinate . . . 1%
Titanium oxide . . . 1%
Insoluble polyvinylpyrrolidone sold under the trade mark Kollidon CL by the Company BASF . . . 25%
Modified cellulose gum, known as Sodium croscarmellose, sold under the trade mark Ac-Di-Sol by the Company Seppic . . . 5%
Glycine . . . 6.5%
Dye . . . 0.2%
Fragrance . . . 0.3%
Sorbitol, sold under the trade mark Neosorb P 60 W by the Company Roquette . . . 13%
Wheat fibers, sold under the trade mark Sofabran F 146 by the company Sofalia . . . 2%
Potato starch . . . 5%
Symperonic PE/F68, sold by the company Lambert-Riviere . . . 2%
Cationic polymer sold under the trade mark N Hance 31 96 by the company Hercules . . . 2%

The compressed tablet obtained exhibits a dis-integration time of approximately 90 seconds in the D test. It remains stable in a moist atmosphere.

When used in a shower, its disintegration time is approximately 1 minute. It produces a more copious foam than the product of Example 1.

We claim:

1. A hair hygiene product for humans or hair treatment product for animals, in a single-dose form, comprising at least one surface active agent selected from the group consisting of an anionic surface active agent and a nonionic surface active agent; an amphoteric product and at least one disintegrating agent, said hair hygiene or treatment product having a disintegration time in an aqueous medium selected from the group consisting of water and aqueous solutions of less than about 5 minutes, wherein the disintegrating agent consists essentially of polyvinylpyrrolidone in amounts from 15% to 40% by weight on a dry basis.

2. The product according to claim 1, wherein the disintegration time is of less than 3 minutes.

3. The product according to claim 2, wherein the disintegration time is of less than 2 minutes.

4. The product according to claim 1, comprising, percentages being expressed by weight on a dry basis:

from 3% to 30% of at least one surface active agent selected from the group consisting of an anionic surface active agent and a nonionic surface active agent;

from 6% to 30% of an amphoteric product; and from 20% to 35% of at least one disintegrating agent.

5. The product according to claim 1, further comprising, percentages being expressed by weight on a dry basis, from 2% to 10% of glycine and from 8% to 25% of a member selected from the group consisting of a granulation excipient and a compression excipient.

6. The product according to claim 5, wherein the compression excipient comprises sorbitol.

7. The product according to claim 1 in a form selected from the group consisting of a pellet and a compressed tablet.

8. A process for the manufacture of a hair hygiene product for man or a hair treatment product for man and animals as defined in claim 1, said process comprising the steps of dry mixing ingredients of a composition and then shaping the ingredients into the product.

9. A process according to claim 8, wherein said shaping step comprises a treatment selected from the group consisting of granulation and direct compression.

* * * * *